United States Patent [19]
Chaussy et al.

[11] Patent Number: 6,022,312
[45] Date of Patent: Feb. 8, 2000

[54] ENDOSPHINCTER, SET FOR RELEASABLE CLOSURE OF THE URETHRA AND METHOD FOR INTRODUCTION OF AN ENDOSPHINCTER INTO THE URETHRA

[76] Inventors: Christian Chaussy, Frunsbergstr. 28, D-82064 Strasslach; Stefan Thüroff, Klausener Platz 23, D-81547 München, both of Germany

[21] Appl. No.: 08/952,313

[22] PCT Filed: May 1, 1996

[86] PCT No.: PCT/EP96/01805

§ 371 Date: Feb. 20, 1998

§ 102(e) Date: Feb. 20, 1998

[87] PCT Pub. No.: WO96/34582

PCT Pub. Date: Nov. 2, 1996

[30] Foreign Application Priority Data

May 5, 1995 [DE] Germany ............. 295 07 519 U

[51] Int. Cl.[7] .................. A61F 2/00; A61M 5/00
[52] U.S. Cl. ........................... 600/29; 604/246
[58] Field of Search .................. 600/29, 30, 31; 604/245, 247, 349, 350

[56] References Cited

U.S. PATENT DOCUMENTS

| 3,818,511 | 6/1974 | Goldberg et al. | 604/8 |
|---|---|---|---|
| 4,932,938 | 6/1990 | Goldberg et al. | 604/96 |
| 5,112,306 | 5/1992 | Burton et al. | 604/101 |
| 5,445,626 | 8/1995 | Gigante | 604/349 |
| 5,667,486 | 9/1997 | Mikulich et al. | 604/8 |

*Primary Examiner*—Cary O'Connor
*Assistant Examiner*—Navin Natnithithadha
*Attorney, Agent, or Firm*—Antonelli, Terry, Stout & Kraus, LLP

[57] ABSTRACT

An endosphincter for the urethra comprising a valve body and a retaining part to secure the valve body in the urethra. The endosphincter can be introduced through the urethral opening into the urethra and retained at a suitable point in the urethra. The retaining part has openings in its jacket wall to secure the valve body in the urethra.

26 Claims, 15 Drawing Sheets

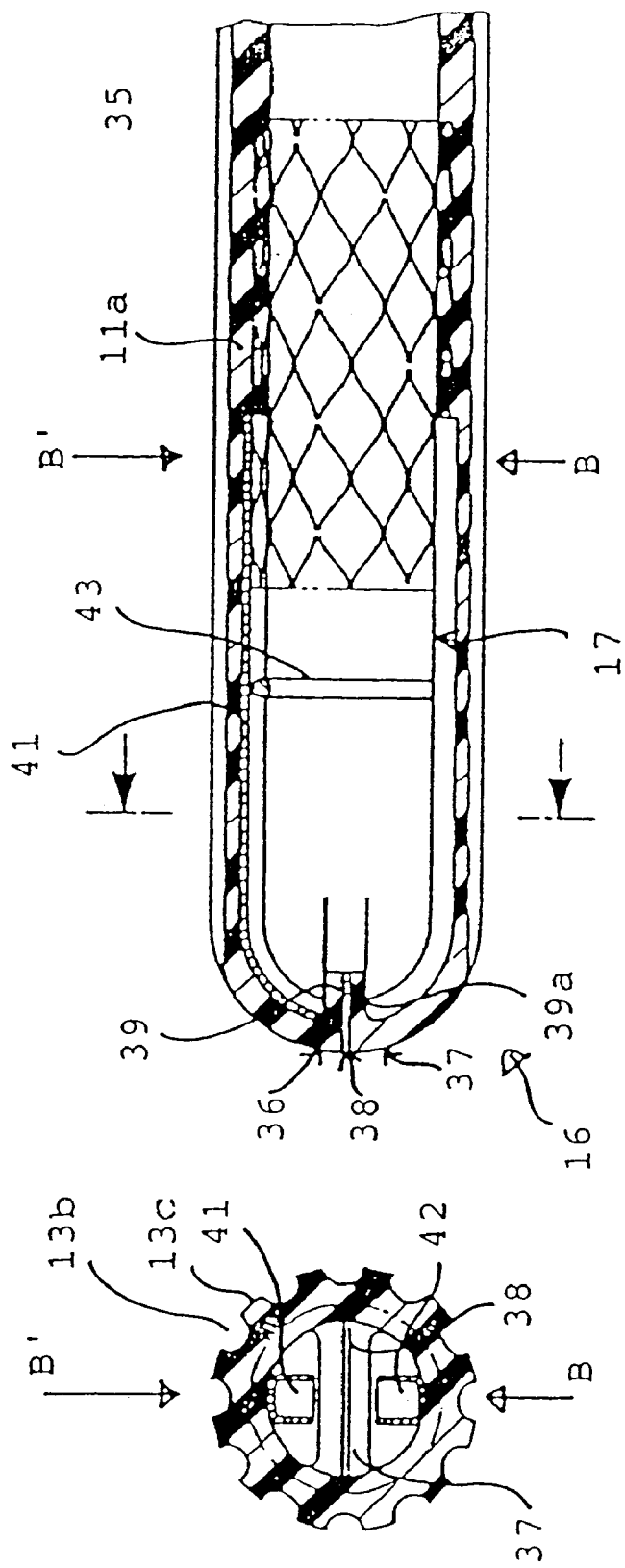

ENDOSPHINCTER, SET FOR RELEASABLE CLOSURE OF THE URETHRA AND METHOD FOR INTRODUCTION OF AN ENDOSPHINCTER INTO THE URETHRA

FIELD OF THE INVENTION

The invention relates to an artificial endosphincter for the urethra, a set for releasable closure of the urethra, and a method for inserting an endosphincter in the urethra.

BACKGROUND AND SUMMARY OF THE INVENTION

Reference is made initially to DE 28 06 405 A1 as the prior art. According to this publication, an artificial sphincter is frequently implanted in cases of urinary incontinence or as a result of injury of removal of the external urethral sphincter following adenectomy of the prostate, radical prostatectomy, neurogenic urinary incontinence, and hyperactivity of the urethral sphincter and congenital urethral muscle defects. In a pneumatic sphincter referred to therein, an inflatable cuff surrounds the urethra so that the cuff can be inflated, preventing the escape of urine through the urethra. The urethra is released by venting the air from the cuff so that the urinary bladder can be emptied. This device must be implanted. A device for pumping air into the inflatable cuff is impractical and burdensome and may often be unsuitable for the user.

In a mechanical sphincter device also referred to, a coil, ring, or torus surrounds the urethra and is deliberately contractible by a control device by the user, preventing the escape of urine. To control the degree of contraction and to avoid adjustment that requires additional surgery involving bleeding, DE 28 06 405 A1, as an improvement on the device described above, provides a device for preventing the closing force from increasing beyond a predetermined closed position to protect the passageway against excessive or harmful closure.

British Patent 1,174,814 teaches an artificial sphincter with a closing body operated pneumatically, hydraulically, mechanically, or electrically, said body being connected directly or indirectly with an actuating device in order to permit actuation of the body to close or open the passageway.

DE 35 21 602 A1 teaches an endourethral sphincter prothesis which is implantable in the prostate cavity that has been cleared. This prosthesis has a short tubular section surrounded by a housing, said section extending from the neck of the bladder to the urethra. To adapt the sphincter prosthesis to the lumen of the empty prostate capsule, a balloon-like bladder made of thin, rubbery material is located around the prosthesis housing, into which bladder rapidly curing silicone foam is injected so that the bladder adjusts to the inside wall of the prostate capsule.

The tube section inside the housing is surrounded by a pressure cuff or a pinch valve. An actuating device is provided for its actuation, said device comprising a hydraulic chamber located in the lower body of the patient, from which chamber a connecting tube extends to a control pump located in the scrotum, from which a tube in turn leads to the cuff or the pinch valve.

It is also disadvantageous in this regard, even if the prosthesis is located in the wound space left by the prostate so that the valve mechanism does not act on the urethra but upon an artificial tubular section, that the entire device must be implanted, i.e. inserted with bleeding. Moreover, it is complex and cumbersome.

The above publication itself also refers to sphincter prostheses according to Rosen with a hydraulically operated clamp acting on the urethra and a prosthesis according to Kaufmann, Kelami-Affeld, and Scott in which a hydraulic cuff in the filled state exerts compression on the urethra, with the actuating elements for controlling the sphincter prosthesis being located out of the way and free of irritation in the scrotum. The subject of DE 35 21 602 A1 includes an improvement on the latter design in order to avoid precisely the disadvantages caused by the action of the valve or clamp on the urethra itself.

EP 348 114 B1 teaches a likewise implantable, i.e. therefore insertable in an operation involving bleeding, artificial closing muscle for a human passageway in the body, more specifically the male urethra. This has a cuff located around the urethra and, when inflated, closes down around the passageway in the body and blocks it, and when it is emptied, allows the body passage to open. The cuff is connected by lines with a pump implantable in the scrotum. A publication —Grein, U., Schreiter, F., 15 Years of Artificial Sphincters —The Schwelmer Results, Z Poster Report —Urology 1/1989, reports on the use of such an artificial sphincter with a sphincter cuff, pressure-regulating chamber, and a pump with control unit, in which activation is accomplished by pressure on the pump implanted in a prepared scrotal pouch or in the labiae majorae. Other previous models are mentioned, the first of which consisted of a reservoir, two pumps, a sphincter cuff, and four valves in tubes between these parts. In another, a pressure-regulating chamber resulted in the elimination of valves. In addition, a reservoir was provided for retarding the fluid flow of the hydraulic system.

These artificial sphincters are implanted by surgery, involving an abdominal incision with incision of the fascia endopelvina adjacent to the prostate and formation of a shallow cavity below the prostate, and after determining the length of the cuff, pulling the latter over the urethra and intraperitoneal installation of the pressure-regulating chamber, placement of the pump in the scrotal pouch or labiae majorae, and finally completion of the tube connections.

In addition, a magnetic urethral closure has been proposed (Z. Urologie 6 (1990)).

The goal of the invention is to provide an artificial sphincter which does not have to be implanted, in other words does not have to be installed by surgery involving bleeding, and in which no additional control devices implanted at other locations in the human body or tubular connections are required. The goal of the invention is also the provision of sets for voluntary closure of the urethra by means of such a sphincter as well as a method for installation of the sphincter.

According to the invention, this goal is initially achieved by an artificial endosphincter for the urethra, which comprises a valve body to be installed in the urethra, with a valve manually operable from the outside by exerting pressure.

The artificial endosphincter according to the invention is inserted through the urethral opening into the latter up to a position, preferably in the vicinity of the natural sphincter to be replaced, i.e. in the vicinity of the pelvic floor, and anchored there by the anchoring part. The self-closing valve located in the valve body is opened by direct actuation from the outside, by exerting radial pressure on the penis from the outside in the vicinity of the valve; for this purpose, the patient for example presses on the penis from above and below. He can thus open the valve and permit the flow of urine. When external pressure is exerted, the valve remains closed so that the urine is retained in the urinary bladder.

In an embodiment with an anchoring part for securing the valve body in the urethra, in a preferred embodiment provision is made such that the anchoring part and valve body are releasably connected with one another. In this embodiment, the anchoring part and valve body can be inserted separately in succession into the urethra so that an epithelium can form initially, after the anchoring part is inserted, over the latter before the valve body is installed in the anchoring part. This embodiment also has the advantage that the valve body, for example if the valve becomes encrusted, can be removed but the necessarily epithelialized anchoring part can remain in the urethra and a new valve body can be inserted and secured in the anchoring part. Alternatively, however, provision can also be made for the anchoring part and valve body to be permanently connected together in such fashion that they cannot be separated without damage.

A highly preferred embodiment provides that the anchoring part comprises a cylindrical main body with a first diameter and at one end a likewise cylindrical end section with a smaller, second diameter, and that the main body and the end section are permanently connected by means of an expanding retaining area for the valve body, with the retaining area being made shoulderwise and especially the retaining area having an expanding area that expands trumpetwise from the end section and a tapering section that is drawn in in the form of an arc from the main body to the expansion section. Provision can also be made in an improvement such that in addition an intermediate section that expands partially conically can be provided between the expanding section and the tapering section.

As a result, a positive connection is produced between the anchoring part and the valve body which, for separation of the latter from the former, with an elastic or flexible design, at least of the tapering and constricted area of the anchoring part and/or the expanding area of the valve body, can be released by applying a greater tensile force. The desired radial flexibility of the anchoring part can be achieved in the preferred embodiment by virtue of the fact that the anchoring part has openings in its jacket wall, with the anchoring part in particular having rhombic openings in its configuration for use. In an alternative embodiment, however, provision can also be made such that the anchoring part is in the form of a coil spring.

Preferably the anchoring part consists of a shape memory alloy such as a nickel-titanium alloy known in one preferred embodiment by the name Nitinol. With such an embodiment, the anchoring part can be inserted, in its low-temperature configuration that has very limited transverse dimensions, into the urethra by means of suitable insertion elements, and expands at human body temperature, which is significantly above the transition temperature of this material, into its high-temperature configuration with larger radial dimensions in which the anchoring part abuts the walls of the urethra and ensures a secure grip there.

An improvement on the endosphincter according to the invention provides that the valve body has a tubular cylindrical main body extending from the retaining area with a smaller diameter than the retaining area. To ensure that no urine can run along the inside wall of the urethra at the edge of the endosphincter and to ensure a sufficiently secure closure, another preferred embodiment provides that the cylindrical main body is provided with sealing lips near the retaining area, whereby in particular the sealing lips extend radially slightly beyond the retaining area.

The invention also includes an anchoring part for securing a functional element such as a valve body in a body passage with the features described above for the anchoring part of the endosphincter according to the invention.

The invention also includes a set for releasable closure of the urethra characterized by an anchoring part and by a valve body connectable with the anchoring part with a valve that is manually operable from the outside by exerting pressure with the valve body being securable in the urethra by the anchoring part. In addition, the device according to the invention includes the provision of a set for releasable closure of the urethra, characterized by a valve body anchorable in the urethra and a device for inserting the valve body into the urethra with a stop as a retainer for the valve body and with an external cannula tube for releasing the valve body, said cannula tube surrounding the stop, receiving the valve body, and being retractable up to the stop.

Another embodiment of a set according to the invention for releasable closure of the urethra is characterized by an anchoring part connected with the valve body and insertable together with the latter in the urethra, whereby in particular a device is provided for initially inserting an anchoring part into the urethra with a retainer for the anchoring part and an external cannula tube for releasing the anchoring part in the urethra, said cannula part surrounding the retainer and receiving the anchoring part, as well as being retractable relative to the retainer. In such an embodiment, additional provision is made such that the diameter of the anterior end of the cannula tube is smaller than the diameter of the end section of the anchoring part or that a guide tube surrounding the valve body and extendable from the outer cannula tube is provided inside the outer cannula tube, said guide tube being divided at its free end into flexible fingers whose free ends are bent toward one another.

A first method for insertion of an endosphincter according to the invention with an anchoring part and valve body permanently connected together provides that insertion elements receiving the endosphincter consisting of a valve body and an anchoring part permanently connected therewith, for insertion of the endosphincter into the urethra, is introduced through the urethral opening into the urethra up to the vicinity of the pelvic floor, and then an outer cannula tube containing the endosphincter is retracted as part of the insertion elements in the direction of the urethral opening relative to a retainer (stop) for the endosphincter, whereupon an anchoring part initially emerges from the outer cannula tube and, because of its intrinsic elasticity, expands radially at human body temperature and becomes anchored in the vicinity of the pars membranacea of the urethra and, with further retraction of the cannula tube, the entire endosphincter is released.

A two-stage method for insertion of an artificial endosphincter into the urethra is characterized in that an inserting element, containing an anchoring part, of a device for insertion of the endosphincter into the urethra is introduced through the urethral opening into the latter up to the vicinity of the pelvic floor, and an external cannula tube containing the anchoring part, with retention of the anchoring part, is released by a retainer in the vicinity of the pelvic floor, so that the anchoring part becomes anchored in the vicinity of the pars membranacea of the urethra as a result of elastic radial expansion at body temperature, and in that, after removal of the insertion elements for the anchoring part, an insertion element containing a valve body is inserted through the urethral opening into the urethra up to an external tapered end section of the anchoring part, and in that a retaining section of the valve body is inserted through the tapered end section of the anchoring part into a retaining area thereof. In an improvement, provision is made such that for insertion of the retaining area of the valve body into the retaining area of the anchoring part, an anterior end area of an outer cannula tube of the insertion element, receiving the valve body, is inserted into the tapered area of the anchoring part and then the valve body together with its retaining area is inserted into the anchoring part or that, to mount the retaining area of the valve body in the retaining area of the anchoring part after insertion of the cannula tube containing the valve body up to the tapered end section of the anchoring part, in its free end area the elastic fingers, bent toward one another, of a guide tube mounted to surround the valve body and located inside the cannula tube are brought out of the cannula tube and inserted into the tapered end area of the anchoring part with the valve body until the retaining area of the valve body reaches the retaining area of the anchoring part and that the cannula tube and the guide tube are then retracted relative to the retainer, whereby initially the retaining area of the valve body inside the retaining area of the anchoring part is released and then the entire valve body is released into the urethra. Insertion of the insertion elements and removal of the anchoring part and/or the valve body are preferably performed under inspection with an endoscope.

Further advantages and features of the invention will follow from the claims and the following specification in which preferred embodiments of the invention are discussed in detail with reference to the drawings.

BRIEF DESCRIPTION OF THE DRAWINGS

FIG. 6b is a cross section corresponding to VI—VI through the embodiment of the valve body with valve according to FIG. 6a;

FIG. 7a is a view corresponding to FIG. 6a with another embodiment of a valve according to the invention;

FIG. 7b is a view corresponding to FIG. 6b of the embodiment shown in FIG. 7a;

FIG. 9b is a section corresponding to FIG. 6a for the embodiment of a valve in FIG. 9a;

DETAILED DESCRIPTION OF EMBODIMENTS

Figure 1B:
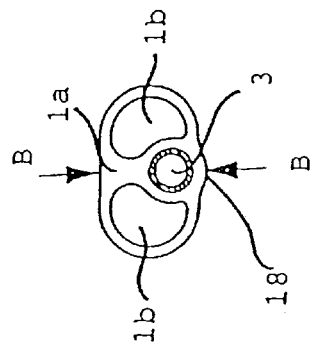
FIG. 1b is a cross section corresponding to IB—IB of FIG. 1a through the penis.
Figure 1A:
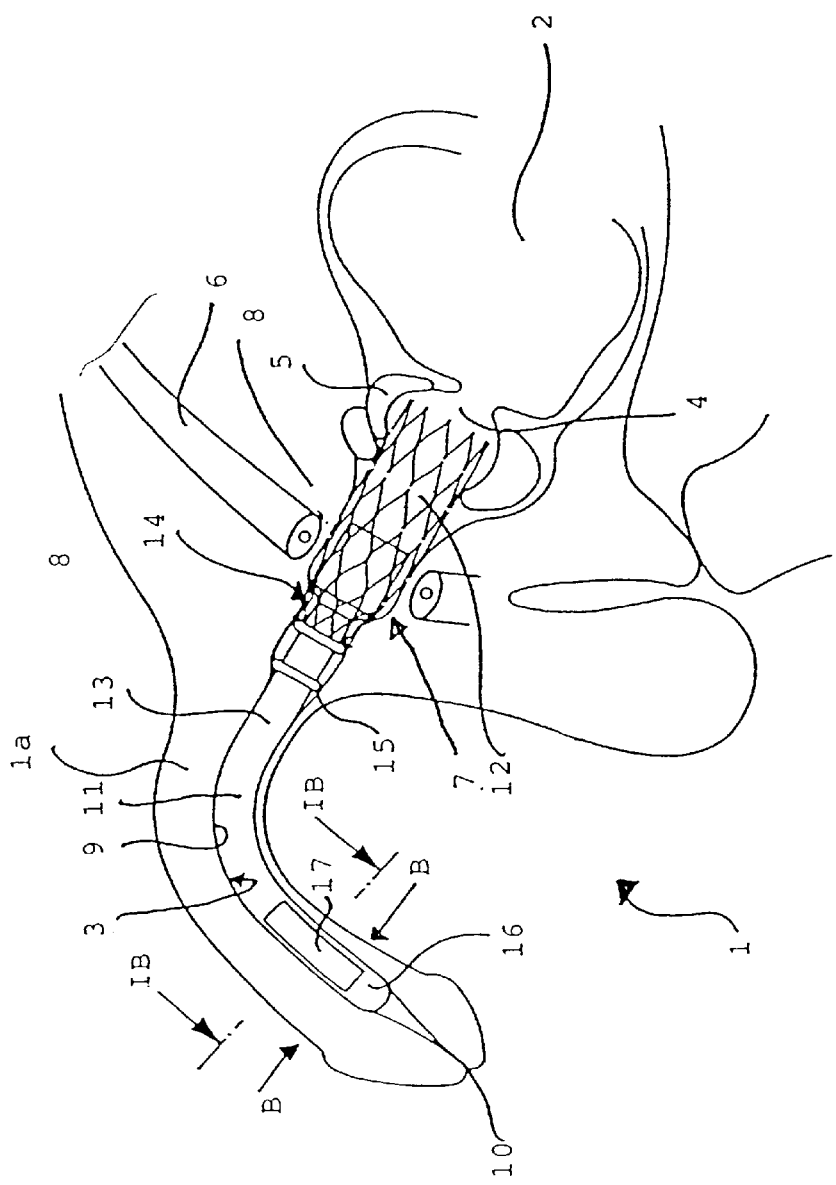
FIG. 1a is a schematic lengthwise section through the male urogenital area, showing an artificial endosphincter according to the invention inserted into the male urethra, in its use position.

FIG. 1a shows a schematic diagram of male urogenital area 1, with an endosphincter according to the invention being inserted through the outer urethral opening into the male urethra.

Urethra 3 extends from bladder 2 to penis 1a with prostatic urethra 4 having a length of about 3 to 4 cm. It is evident that at least a portion of prostate 5 has been removed. Reference numeral 6 represents the diaphragma urogenitale, which is part of the pelvic floor, penetrated by the pars membranacea 7 with a length of approximately 1 to 2 cm, which in turn is usually surrounded by the outer sphincter 8 (musculus sphincter urethrae). The pars membranacea 7 of urethra 3 is adjoined by its pars spongiosa 9 in the corpus spongiosum, which eventually terminates at the outer urethral opening 10 (ostium urethrae externum). Urethra 3 is located in the lower portion of penis 1a, below and between the corpora cavernosa 1b.

In the patient whose urogenital area 1 is shown in FIG. 1a, because of removal of or injury to external sphincter 8 or hyperactivity of the latter, an artificial endosphincter 11 has been installed according to the invention, as shown in its use position in FIG. 1a.

Endosphincter 11 has an anchoring part 12 which contains a valve body 13. Anchoring part 12 is located inside at the position of outer sphincter 8, in other words in the vicinity of the pars membranacea 7. The exact position depends on the individual situation. Valve body 13 extends into pars spongiosa 9 from anchoring part 12.

Valve body 13 has, near its inner end 14 held by anchoring part 12, sealing lips 15, whereby in the embodiment shown, two sealing lips are provided which project radially beyond valve body 13. Valve body 13 is made in the form of a hollow tube with a jacket wall 13a. In external end area 16 that faces away from anchoring part 12, a valve 17 is provided which can be designed in various ways and is explained in detail below. Endosphincter 11 is provided in urethra 3 in such fashion that valve 17 can be opened by exerting pressure from the underside of penis 1a (in the vicinity of raphe penis 1a formed by the growing together of the genital furrow and on the dorsal surface of penis 1a in the direction of arrows B and B' respectively.

As long as no pressure is exerted on valve 17, the valve remains closed. The urine is retained in urinary bladder 2 and in valve body 13; the patient is therefore continent thanks to endosphincter 11 according to the invention, but can open this sphincter by exerting pressure as described on valve 17, thus releasing urine.

Figure 2:
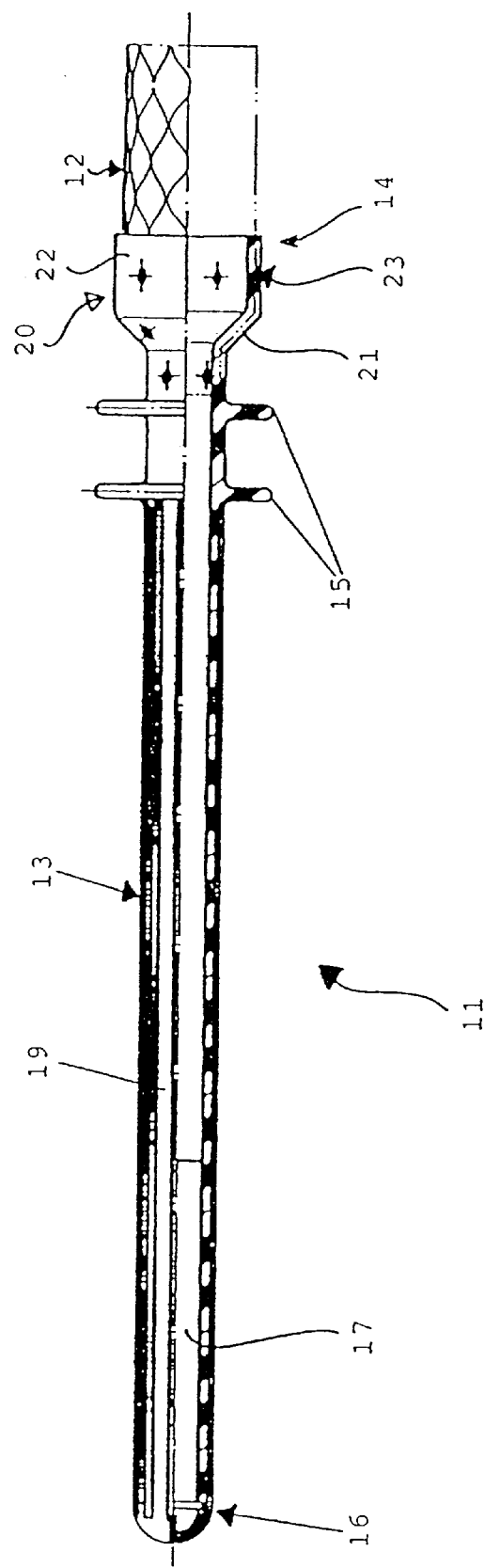
FIG. 2 shows a first embodiment of an endosphincter according to the invention, with the valve merely being shown schematically.

FIG. 2 shows a first embodiment of the endosphincter 11 according to the invention. In this embodiment, valve body 13 and anchoring part 12 are permanently connected together in such fashion that they cannot be separated from one another without damage. Valve body 13 has a cylindrical main body 19 in whose anterior or outer end area 16, as stated, valve 17 is inserted. On the outer circumference of a jacket wall 13a of valve body 13, lengthwise grooves 13b are provided between lengthwise ribs 13c. The lengthwise grooves serve as drain grooves to conduct away the secretion that forms in the urethra to the outlet of the ureter. Cylindrical main body 19 expands in a retaining area 20 by means of a shoulder 21 to a likewise cylindrical end section 22. Main body 19 therefore has a first diameter that is smaller than the diameter of end section 22. In an area of main body 19 that is close to end section 22, the main body is surrounded by elastic sealing lips 15. The diameter of elastic sealing lips 15 is on the order of magnitude of end section 22, preferably slightly larger than the diameter of end section 22. In the design shown in FIG. 2, in end section 22, shoulder 21 and a short part of main body 19, a retaining area 23 of anchoring part 12 is inserted or cast. Valve body 13 preferably consists of silicone or relatively soft plastic material, anchoring part 12 consists of a perforated structure made of metal, and especially of a shape memory alloy such as a nickel-titanium alloy; one such alloy is known as Nitinol. In this case, the anchoring part, at relatively low temperatures, especially temperatures significantly below body temperature of 37° C., has a shape with a small diameter and expands only above a transition temperature that is likewise below body temperature, into its high-temperature shape with a relatively large diameter, as shown in FIGS. 1 and 2.

Endosphincter 11 according to FIG. 2, in which therefore anchoring part 12 and valve body 13 are permanently connected together, is inserted together as such through ureter opening 10 into urethra 3.

Figure 3:
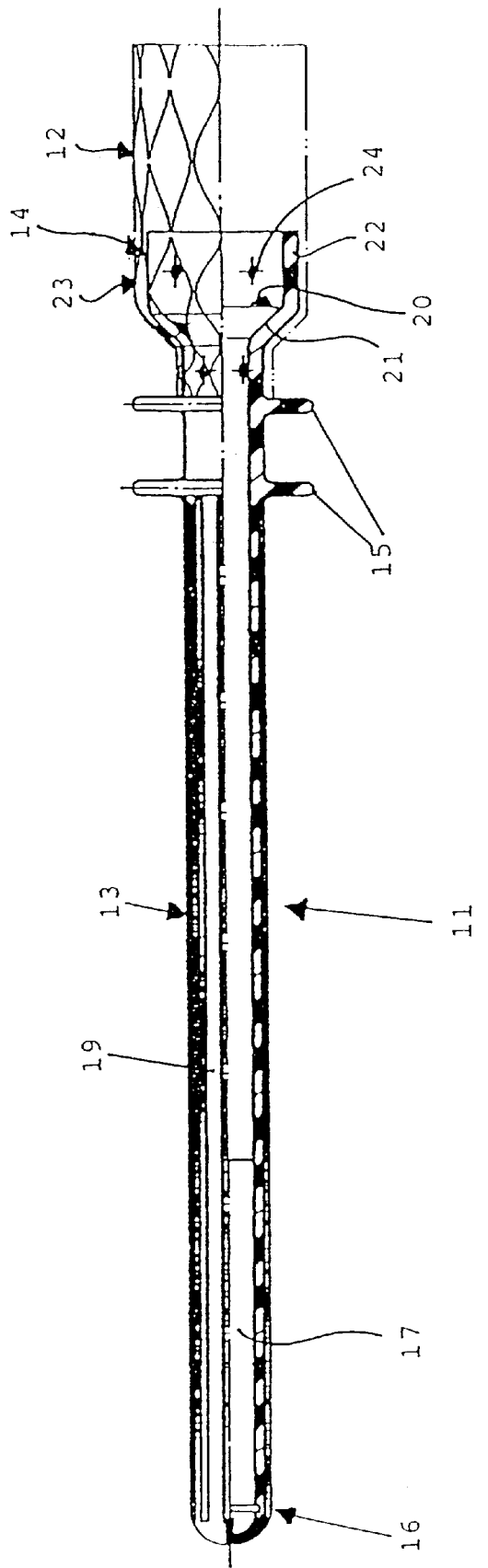
FIG. 3 shows another embodiment of the endosphincter according to the invention with a releasable anchoring part and valve body in the assembled use state.

FIG. 3 shows another embodiment of endosphincter 11 according to the invention in its use state. The same parts have been given the same reference numerals.

In the embodiment shown in FIG. 3, valve body 13 and anchoring part 12 are releasably connected together, with retaining area 20 or the head of valve body 13 being held positively inside retaining area 23 of anchoring part 12. Since both anchoring part 12 and valve body 13 and especially retaining area 20 are made flexible and elastic, valve body 13 may be separated and removed if desired from anchoring part 12, so that a simple replacement of valve body 23 alone is possible when the latter for example has become encrusted, while anchoring part 12 remains in its position as shown in FIG. 1, in the urethra membranacea. This is extremely advantageous since anchoring part 12 has be come overgrown by epithelial tissue.

Valve body 13, especially in end area 22 and in its area between the latter and the first sealing lip, has drainage openings 24.

Figure 4A:
FIG. 4a shows a first highly preferred embodiment of the anchoring part in its radially compressed insertion configuration.
Figure 4B:
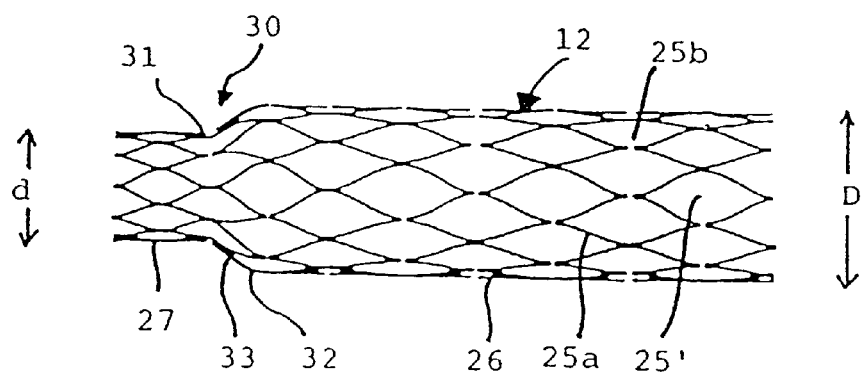
FIG. 4b shows the anchoring part of FIG. 4a in the radially expanded use configuration.

A highly preferred embodiment of an anchoring part 12 of endosphincter 11 according to the invention is shown in FIGS. 4a and b. FIG. 4a shows the insertion or low-temperature configuration of anchoring part 12 with a very small diameter while FIG. 4b shows the insertion contour or high-temperature contour. Anchoring part 12 consists of a very thin sheet with a plurality of slits or cuts 25 arranged successively in its main direction of extent and arranged staggered around the circumference. In the high-temperature position, these cuts expand to rhombic openings 25'.

The ribs 25a that delimit slits 25 or openings 25' are partially cut open (cuts 25b); this produces a high angular bending flexibility of anchoring part 12.

The outer contour of anchoring part 12 in the high-temperature position shown in FIG. 4b is as follows: Anchoring part 12 has a cylindrical main body 26 with a first diameter that corresponds mainly to the diameter of end section 22 of valve body 13. Anchoring part 12 also has a likewise cylindrical end section 27 that has a smaller diameter than main body 26. Between section 27 and main body 26, retaining area 30 is provided, said area expanding from the former to the latter.

Retaining area 30 is designed to expand shoulderwise. Beginning at end section 27, it initially has a first expansion section 31 that expands trumpetwise and then a tapering section 32 that is constricted arcwise or tapering from main body 26 to expansion section 31. In the embodiment shown, a partially conically expanding intermediate section 33 is provided between sections 31 and 32.

Figure 5:
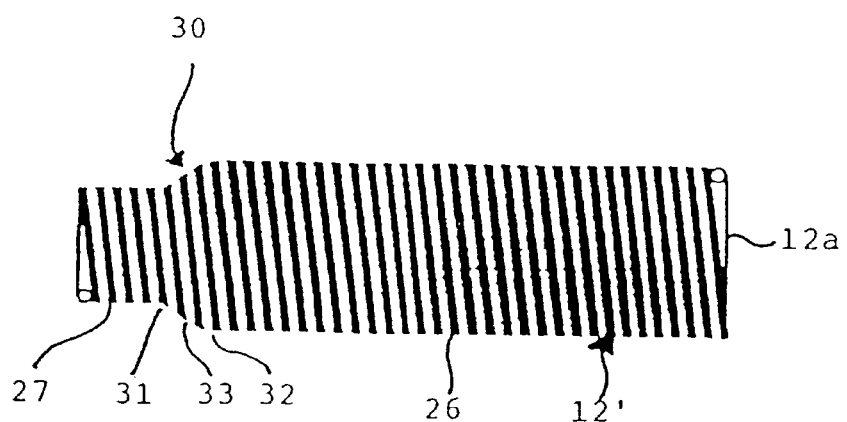
FIG. 5 is a schematic diagram of another embodiment of an anchoring part according to the invention.

FIG. 5 shows another embodiment of an anchoring part 12' according to the invention formed by a helically coiled wire and in which basically the same sections are provided as in the embodiment of FIGS. 4a and 4b. In addition, wire 12a of anchoring part 12' consists of a shape memory alloy (memory metal alloy) of the species described above and likewise has a low-temperature position with a very small diameter.

Figure 6A:
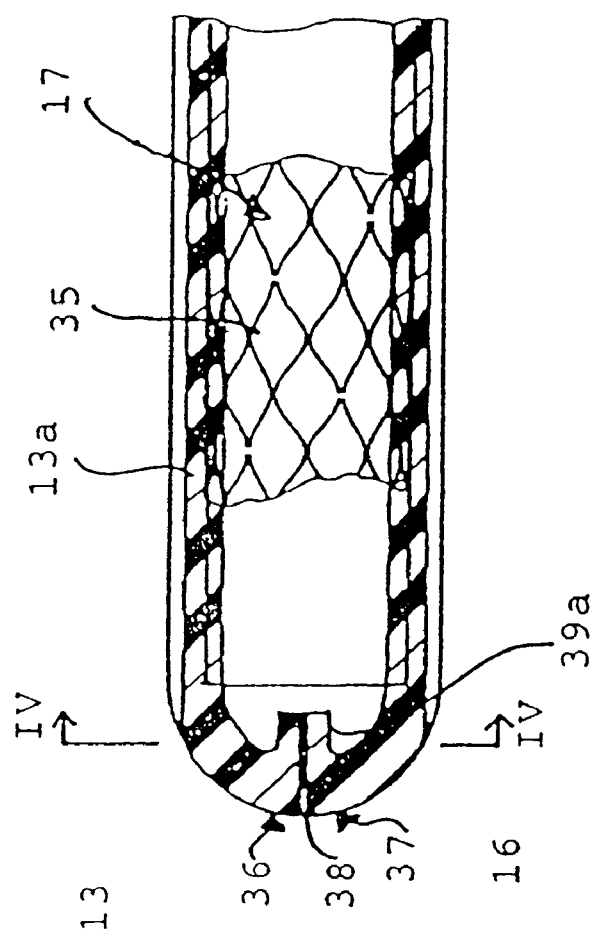
FIG. 6a is a schematic diagram of a first embodiment of the anterior or outer end of the valve body, with the valve located therein, in lengthwise section.
Figure 6B:
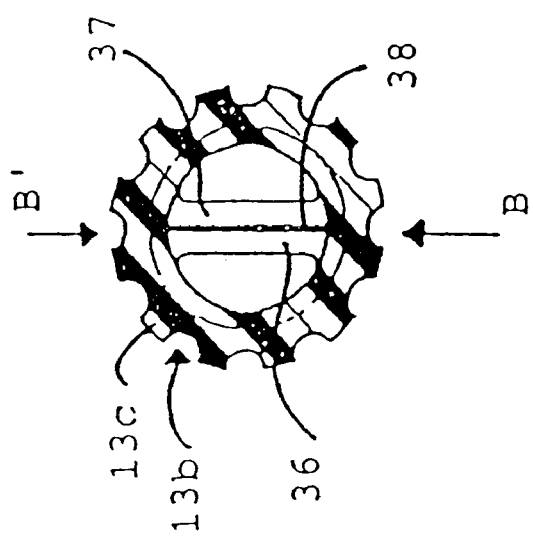

FIGS. 6a and 6b show a first embodiment of valve body 13 of endosphincter 11 according to the invention.

In the embodiment of FIGS. 6a and 6b, valve 17 has a flexible elastic cylindrical jacket part 35 fitted into jacket 13a of valve body 13. For clarity, an inner wall area of jacket 13a of valve body 13 has been cut away partially so that the inserted cylindrical jacket part 35 is clearly visible. Likewise, it can be provided preferably with openings such as rhombic openings similar to those in the embodiment of FIG. 4b of anchoring part 12. Cylindrical jacket part 35 preferably consists of corrosion-free stainless steel.

The outer end area 16 of valve body 13 is rounded endwise and provided with two vertically directed sealing lips 36, 37 which enclose a slit opening 38 between them. Sealing lips 36, 37 are provided with projections 39, 39a directed toward the interior of valve body 13. In the unloaded state, sealing lips 36, 37 tightly close off slit opening 38 that is shown stretched here, so that no liquid can escape from the interior of valve body 13. When pressure is exerted in the direction of arrows B, B', in other words perpendicular to the extension direction of slit 38, on outer end area 16 of cylindrical body 35, sealing lips 36, 37 are forced apart so that slit opening 38 opens and liquid can escape from the interior of valve body 13 into the urethra and from its outer opening.

In the embodiment in FIGS. 7a and 7b, an elastic cylindrical body 15 is likewise provided. This body however is located at a greater distance from the anterior end 16 of the valve body. It is provided on the upper and lower surfaces with levers 41, 42, with lever 41 extending inside wall 13a of valve body 13 up to projection 39 of sealing lip 36, while the lever extends in the same manner up to a point below projection 39 of sealing lip 37. Between projections 39, 39a and elastic body 35, a hinge part 43 is provided that is permanently connected with levers 41, 42 but is itself elastic.

By means of this embodiment, when pressure is exerted in the direction of arrows B, B' on the ends of levers 41, 42 that are located on the outside of elastic body 35 by lifting on the opposite ends that are located in end 16 of valve body 13, slit 38 is opened hinge part 43 then bends slightly. A greater lever action can be achieved in contrast to the embodiment shown in FIGS. 6a, 6b. The pressure direction relative to the extension direction of slit opening 38 differs, here being perpendicular to the extension direction while in the embodiment shown in FIGS. 6a and 6b the pressure was exerted in the extension direction of slit opening 38; relative to the human body or penis however, the pressure must always be exerted from above and below, as stated above.

Figure 8:
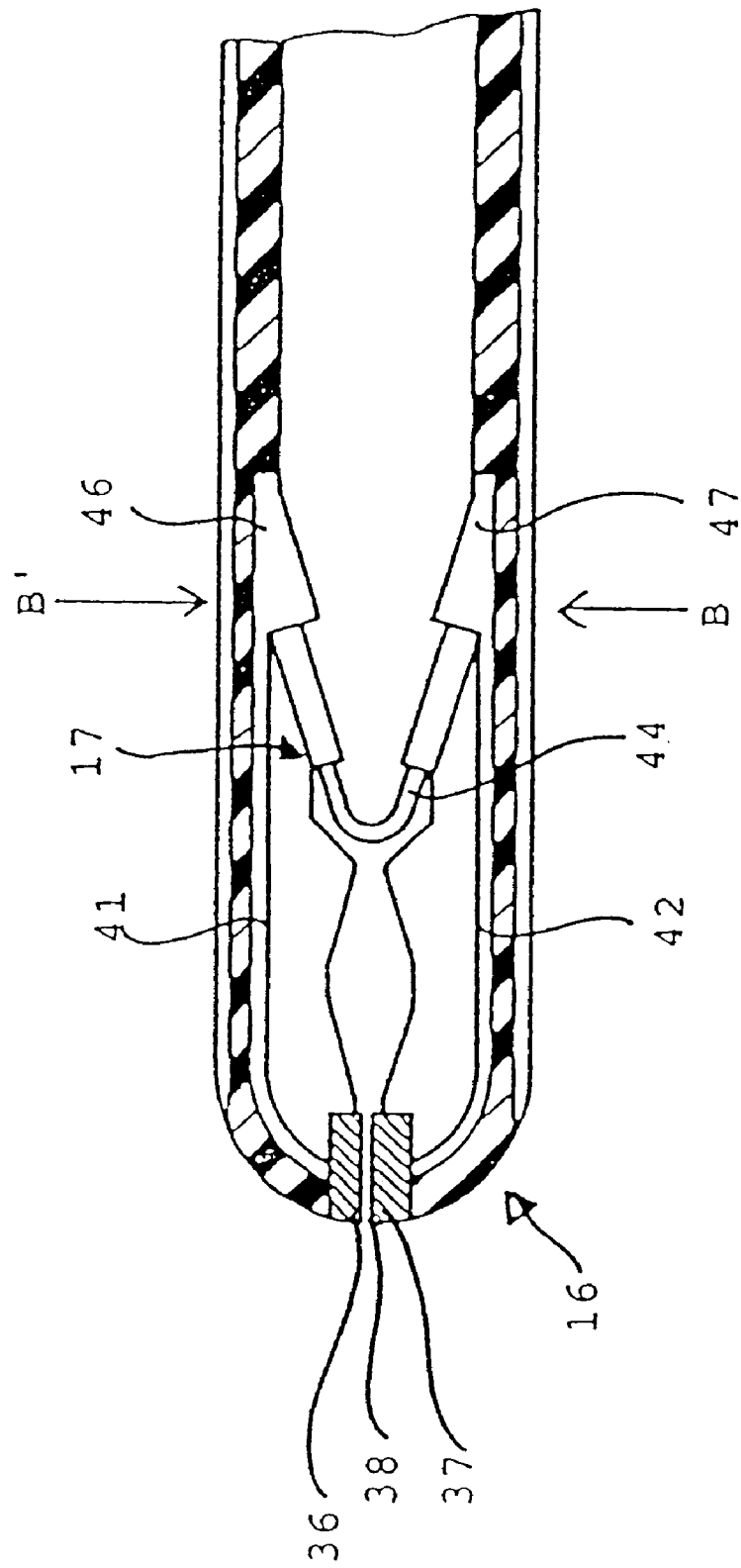
FIG. 8 is another embodiment of a valve according to the invention in the anterior part of the valve body.

Another embodiment of a valve according to the invention is shown in FIG. 8. This embodiment likewise operates with two-armed levers 41, 42 corresponding to the embodiment in FIGS. 7a and b. The elastic restoring part that in the embodiment in FIGS. 6a, 6b, 7a, and 7b was a cylindrical elastic body, is here replaced by a bow-shaped spring 44, which engages in the vicinity of the inner ends 46, 47 of levers 41, 42 and extends in a V-shaped manner toward end 16 up to about the middle of the length of lever 41, 42. The latter also in turn engage above and below sealing lips 36, 37, which in this case are not made integral with walls 13a or the jacket of valve body 13, but are inserted as separate parts in anterior end 16. The valve is likewise actuated in the direction of arrows B, B' in the vicinity of ends 46, 47 of levers 41, 42, which thus act as actuating surfaces.

Figure 9A:
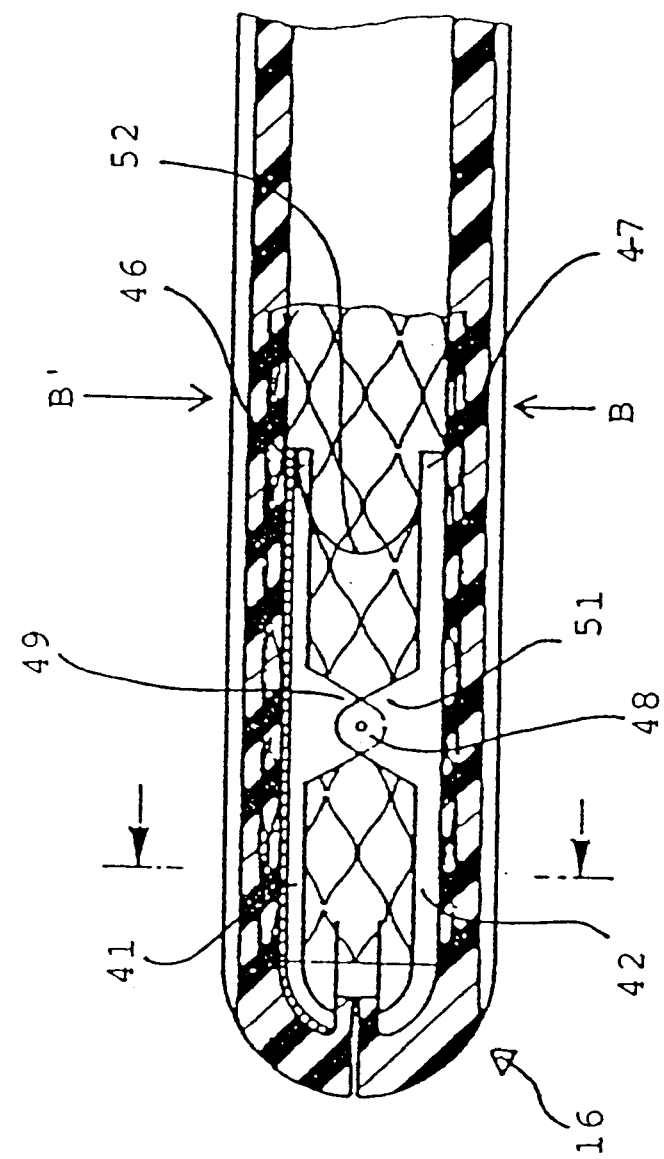
FIG. 9a is likewise a lengthwise section through another embodiment of the valve according to the invention in the anterior area of the valve body.
Figure 9B:
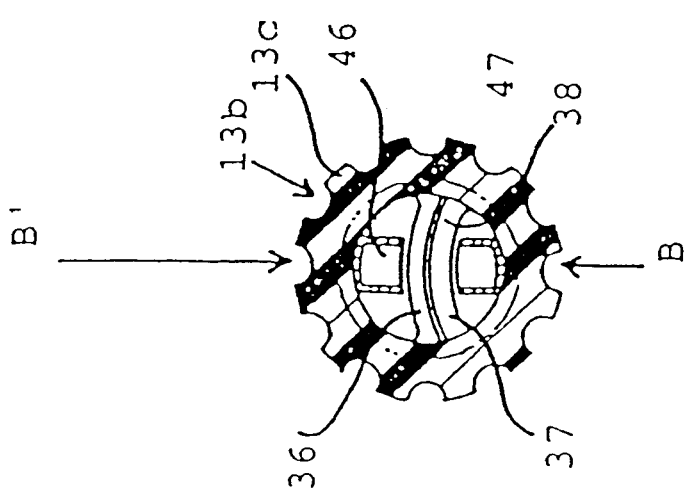

In the embodiment shown in FIGS. 9a and 9b, two-armed levers 41, 42 are likewise provided once more. These levers have a pivot joint 48 on two articulated bearing parts 49, 51 moved toward one another by levers 41, 42. A bow spring 52 is located as a restoring element between ends 46, 47 of levers 41, 42 facing away from end 16. In addition, as shown, a flexibly elastic cylindrical jacket part 35 can also be provided as shown for stiffening the cylindrical main body 19 of valve body 13 in wall 13a, as in the embodiments of FIGS. 6a, 6b, 7a, and 7b.

Slit opening 38 is made arc-shaped here, as can be seen in FIG. 9b.

When pressure is exerted in the arrows B, B' in the vicinity of ends 46, 47, levers 41, 42 pivot around pivot joint 48 and also open slit opening 38.

It should also be stated in connection with the embodiments of the valve explained with reference to FIGS. 6a to 9b that individual elements of one embodiment can also be combined with other elements of another embodiment, so that for example the curved slit opening 38 of the embodiment in FIGS. 9a and 9b can be used in the valve designs of the other figures that have been explained and in the embodiment of FIG. 9a, a straight slit corresponding to FIGS. 6b and 7b may be used.

Figure 10:
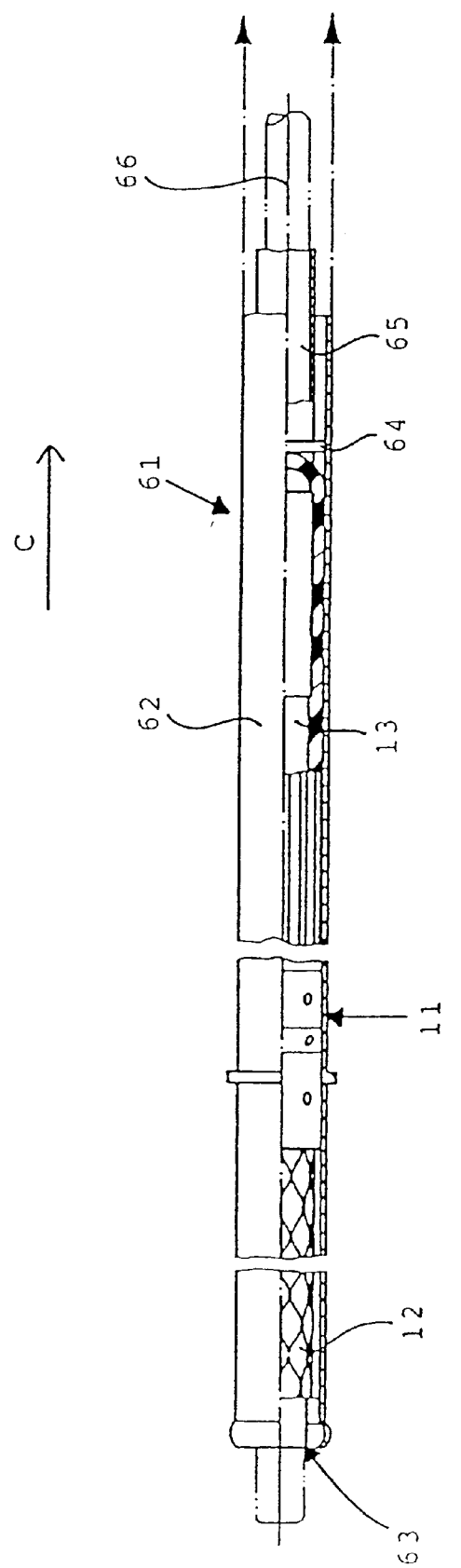
FIG. 10 is a view of the insertion elements for an endosphincter according to the invention corresponding to FIG. 2a with the endosphincter inserted.

FIG. 10 shows insertion element 61 that can be inserted into the urethra for an endosphincter 11 according to the invention in the embodiment of FIG. 2, in which anchoring part 12 and valve body 13 are permanently connected together in the manner shown there. Insertion elements 61 initially have an outer cannula tube 62 in which endosphincter 11 with valve body 13 and anchoring part 12 is held with radial contraction. Anchoring part 12 is located near outlet opening 63 of cannula tube 62. On the end 22 of valve body 13 that is facing away from anchoring part 12, stop 64 of a second inner cannula tube 65 abuts. Through the entire system and therefore also through cannula tube 62 there extends an optical fiber 66 of an endoscope, for which purpose the valve (not shown) of valve body 13 is opened very slightly.

Outer cannula tube 62 and inner cannula tube 65 are movable relative to one another, more specifically outer cannula tube 62 can be retracted relative to inner cannula tube 65 in the direction of arrow C. For this purpose, cannula tubes 62, 65 can be provided at their ends facing away from removal opening 63 with actuating devices as described for example in P 44 20 142 A1, which are expressly mentioned and whose subject has been made the subject of the present application.

The insertion of an endosphincter according to the invention with the design according to FIG. 2 is accomplished in the following fashion: initially, insertion element 61 with the endosphincter placed in cannula tube 62 corresponding to the design in FIG. 10, is introduced through opening 10 in urethra 3 into the latter. The removal opening 63 of cannula tube 62 is then pushed up to the diaphragma genitale and/or pelvic floor 6. During this insertion of insertion element 61, cannula tubes 62, 65 do not change their relative axial positions. The exact positioning can be observed by optical fiber 66 of the endoscope.

Figure 11:
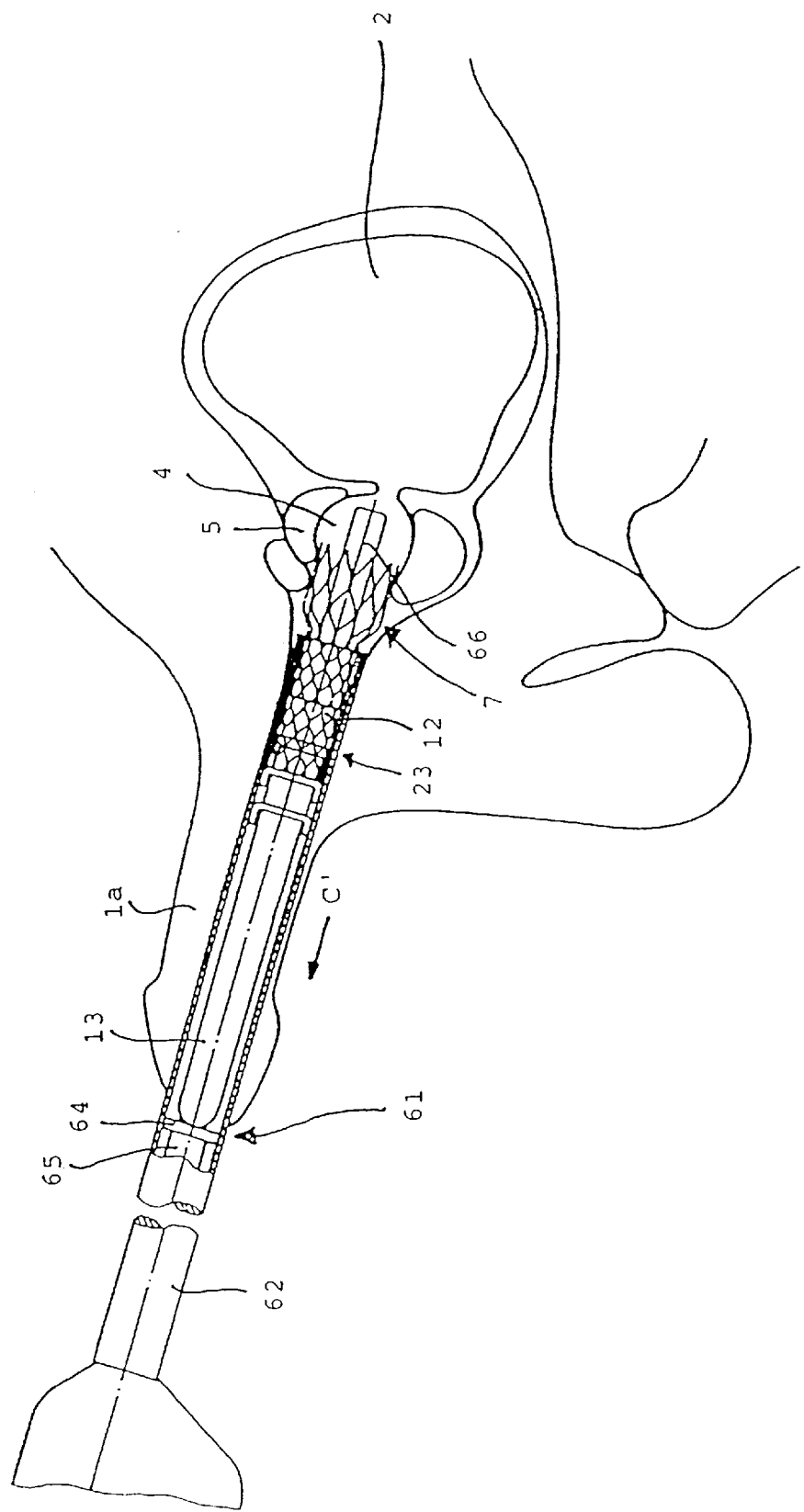
FIG. 11 shows the important method step of releasing the endosphincter in FIG. 2a from the insertion elements of FIG. 10, into the urethra in the vicinity of the pelvic floor.

Then the outer cannula tube 62 is retracted in the direction of arrow C (FIGS. 10 and 11), namely relative to inner cannula tube 65, which with its stop 64 abuts end 16 of endosphincter 11 as a retainer. As a result, initially anchoring part 12 is released in the vicinity of pelvic floor 6 from removal opening 63 of outer cannula tube 62, as shown in FIG. 11. As outer cannula tube 62 is retracted further in the direction of arrow C, the entire endosphincter and especially its valve body 13 as well are gradually released until the outer end area 16 of valve body 13 is likewise released from the outer cannula tube 62. Then insertion elements 61 can be removed from the urethra through urethral opening 10.

Endosphincter 11 according to the invention with the design according to FIG. 2 is installed in this fashion and can be used in the manner described. Provided its valve is not subjected to pressure, it retains the urine; by applying stress, in other words exerting pressure in the direction of arrows B, B', the patient's bladder can be drained in the manner described.

Figure 12:
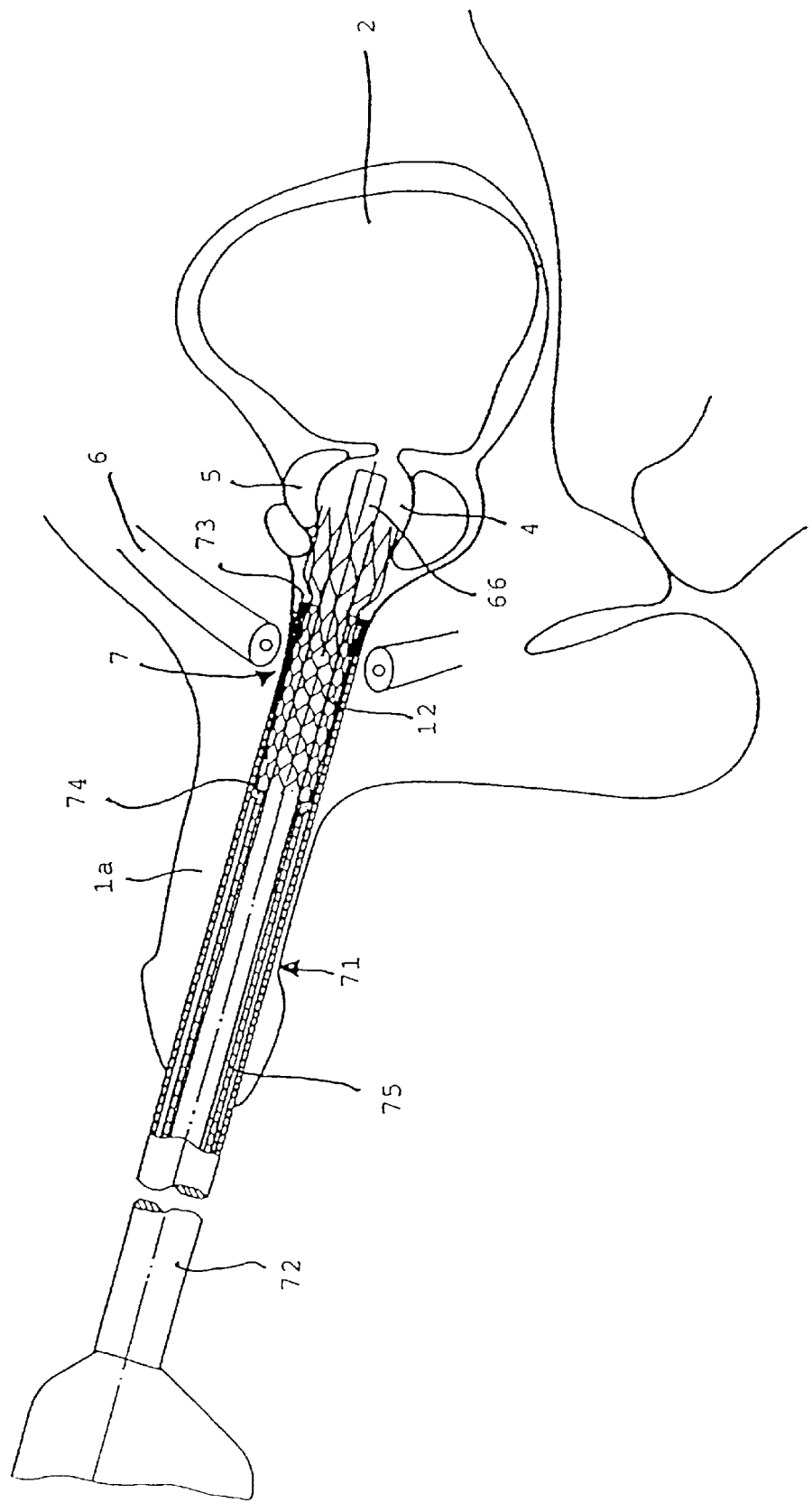
FIG. 12 shows insertion elements for the anchoring part in FIGS. 4a and 4b of an endosphincter according to FIG. 3 in the position in which the anchoring part is released into the urethra in the vicinity of the pelvic floor.

FIG. 12 shows the important insertion elements 71 of an insertion instrument for insertion initially only of anchoring part 12 of the embodiment shown in FIG. 3 of endosphincter 11 according to the invention in which anchoring part 12 and valve body 13 are releasably connectable with one another. Here too, initially an external cannula tube 72 and an inner cannula tube 75 serving as a stop or retainer is provided. The removal opening of outer cannula tube 72 is marked 73. Inner cannula tube 75 has its end 74 abutting the outwardly directed end of anchoring part 12. Fiber 76 of an endoscope, not shown in greater detail, extends through the entire system. Insertion elements 71 are also connected at their ends facing away from removal opening 73 by a mechanism for relative movements thereof. For insertion of insertion elements 71, anchoring part 12 is first pushed all the way into outer cannula tube 72. Insertion elements 71 are introduced in the manner described above with reference to FIG.

11 into urethra 3 until removal end 73 of outer cannula tube 72 has passed through pelvic floor 6. Then outer cannula tube 72 is retracted, with retention of inner cannula tube 75, relative thereto in the direction of arrow C, so that anchoring part 12 is released and can position itself in urethra 3, especially in its pars membranacea 7. The insertion elements are finally withdrawn completely from the urethra.

As a rule, formation of epithelium on anchoring part 12 is initially awaited before valve body 13 is introduced.

Figure 13:
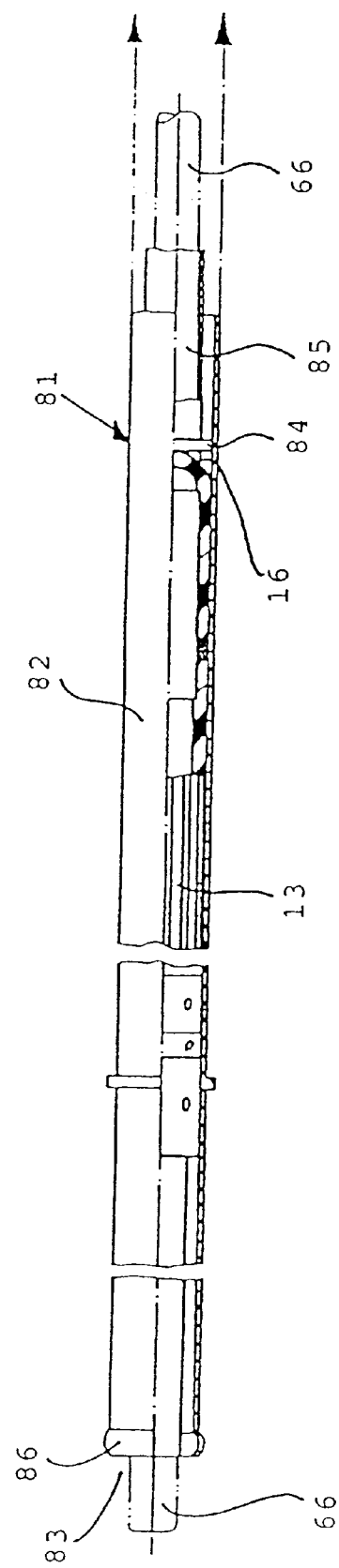
FIG. 13 shows the insertion elements for insertion of the valve body of the design according to FIG. 3 for the endosphincter according to the invention.
Figure 14:
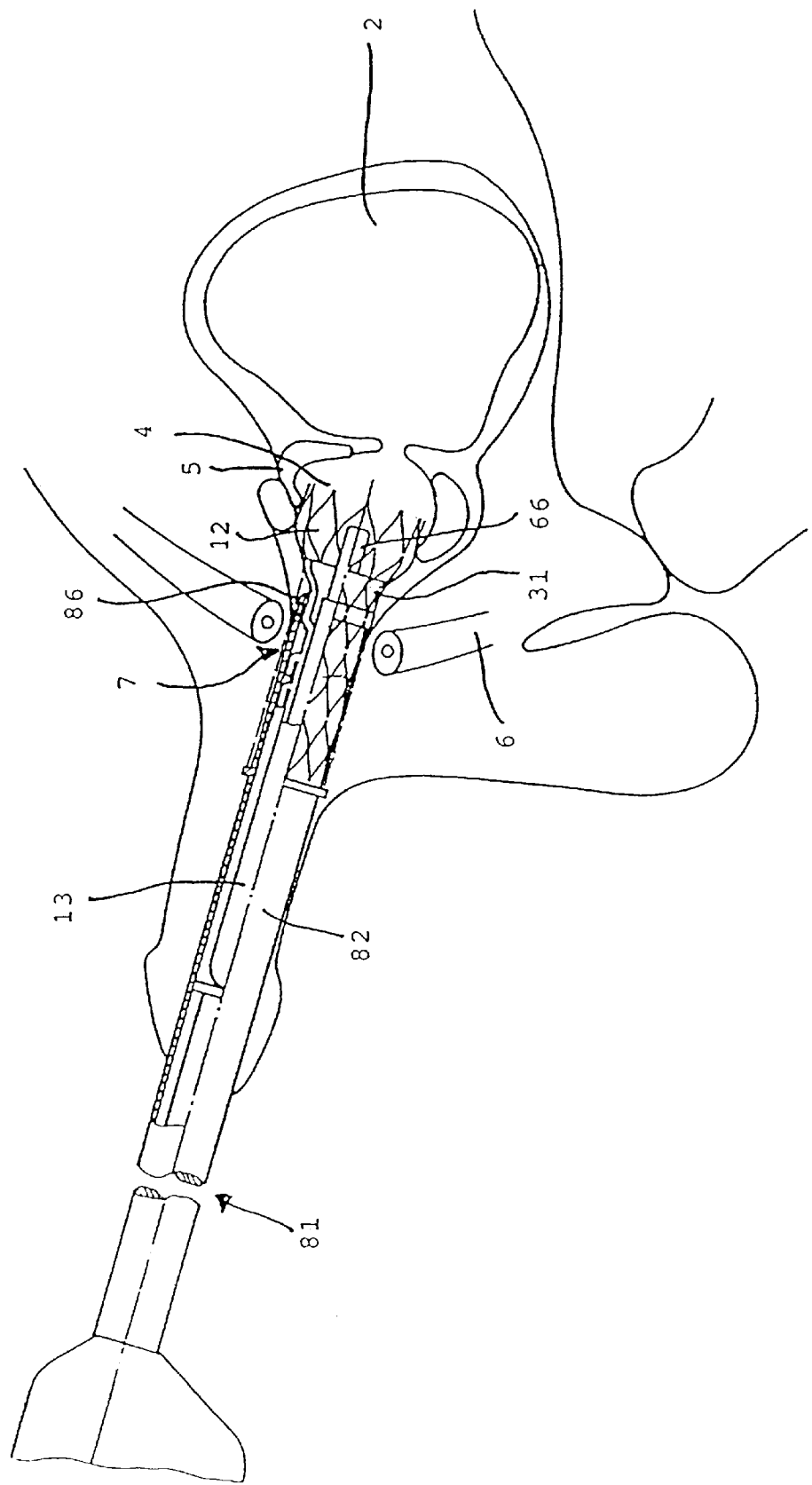
FIG. 14 shows the important method step of inserting the valve body by means of insertion element 81 into the previously inserted anchoring part of the design shown in FIGS. 3, 4a, and 4b.

FIG. 13 initially shows a first embodiment of the important insertion elements 81 for a valve body 13 according to FIG. 3. The embodiment of insertion elements 81 is essentially similar to that of the insertion elements 61 described in FIG. 10. An outer cannula tube 82 with a removal opening 83 is provided. In outer cannula tube 82 there is an inner cannula tube 85, as a retainer movable with respect to said tube, with a stop 84 abutting the outer end area 16 of valve body 13. Once again a fiber optic 66 extends through the entire system. Outer cannula tube 82 has its removal opening 83 surrounding a rounded insertion section 86. The diameter of insertion section 86, which is tapered in slightly arcuate fashion toward the free end, lies below the inner diameter of anchoring element 12 in its tapered cylindrical end area 27 in the relaxed state of anchoring element 12, in other words when the latter has assumed its expanded or high-temperature contour, as shown in FIG. 4 as well as FIG. 14.

For insertion of insertion elements 81 into urethra 3 of a patient, valve body 13 is once again located completely in outer cannula tube 82, as shown in FIG. 13. Insertion of insertion elements 81 into urethra 3 basically also takes place in the manner described above.

When end 86 of outer cannula tube 82 reaches a point in front of anchoring part 12, it is introduced while being viewed into the tapered cylindrical end 27 of anchoring part 12, which is possible because of the diameter ratios described. Outer cannula tube 82 is brought out by its end 86 beyond area 32 of anchoring part 12. Throughout the entire insertion process, the relative positions of outer cannula tube 82 and inner cannula tube 85 are retained. Then outer cannula tube 82 is retracted once more relative to inner cannula tube 85, so that initially the expanded retaining area 23 of valve body 13 is released so that it can abut area 12 of anchoring part 12.

Then outer cannula tube 82 is retracted successively further so that the entire valve body 13 is released until it is completely free inside urethra 3 and is held in place by anchoring part 12. The insertion elements are removed from the urethra. Valve 17 of valve body 13 can then be used in the manner described above to control urine flow.

Figure 15:
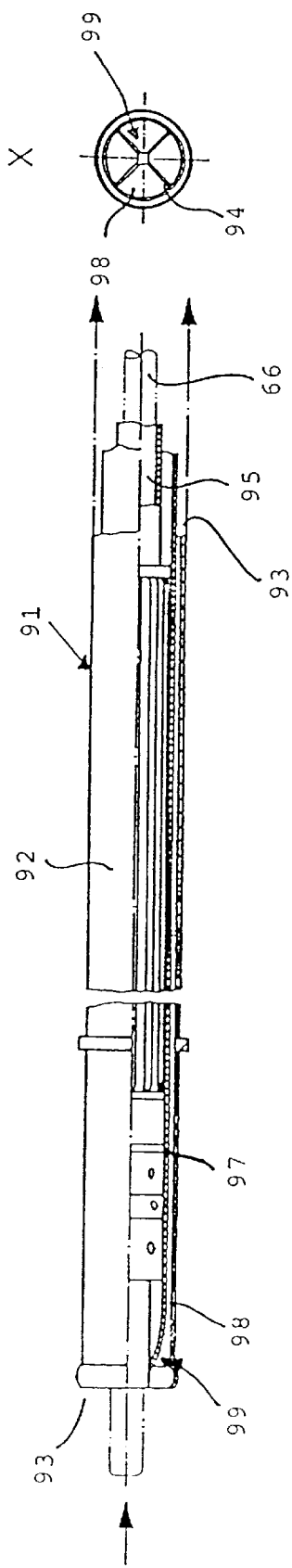
FIG. 15a is a partial lengthwise section through another embodiment of the insertion elements for insertion of the valve body of the design shown in FIG. 3 for the sphincter according to the invention into the previously installed anchoring part.
FIG. 15b is an end view of the subject of FIG. 15a before the valve body is removed.
Figure 16:
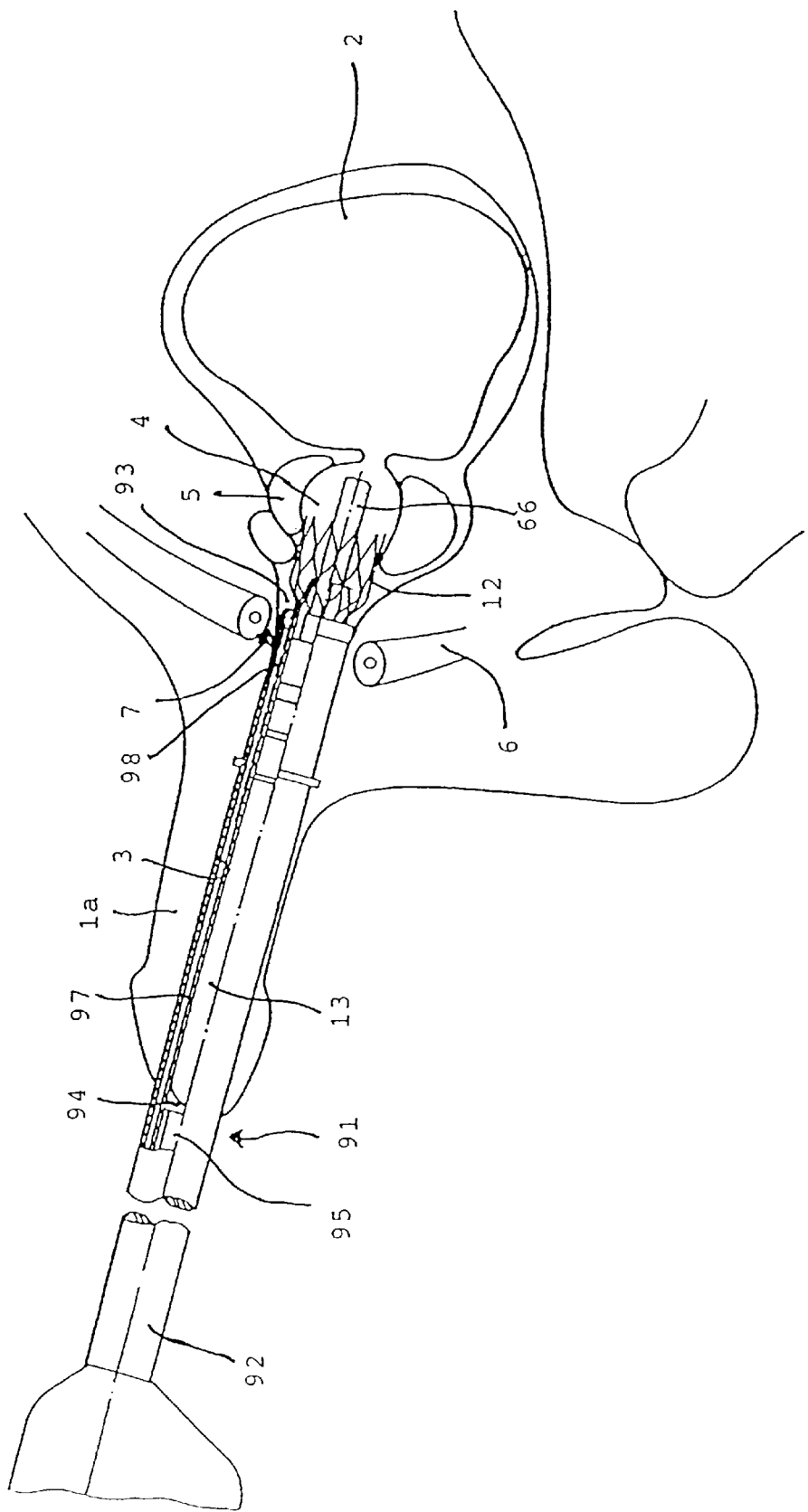
FIG. 16 shows the important method step for insertion of the anchoring area of the valve body into a previously installed anchoring part.

FIG. 15 shows insertion elements 91 of a revised embodiment of an insertion instrument. The diameter of outer cannula tube 92 is once again greater than the diameter of part 27 of anchoring part 12. In order nonetheless to permit insertion of end 22, 23 of valve body 13 into anchoring part 12, whose end 27 has a smaller diameter than parts 22, 23 of valve body 13 in the radially relaxed state, insertion elements 91 have a guide tube 97 between the wall of outer cannula tube 92 and valve body 13. Guide tube 97 is divided at its forward end facing removal opening 93 for a sufficient length into four fingers 98. Fingers 98 and hence guide tube 97 taper toward opening 93 into a blunt end area 99. Fingers 98 are relaxed, and when they are not held together by radial pressure from outside (as in this case initially by cannula tube 92), they are bent radially outward and open a discharge opening by the application of force from the inside (by valve body 13 in a manner to be described below).

The other parts of insertion elements 91 in this embodiment are the same as those in the embodiment in FIG. 13. External cannula tube 92 and inner cannula tube 95 are movable axially relative to one another. In addition, guide tube 97 is movable relative to the two cannula tubes 92, 95.

The insertion of insertion elements 91 into urethra 3 occurs in the manner described above relative to the other embodiments of the insertion elements, with viewing through the above-mentioned endoscope. When the discharge end 93 of cannula 92 has arrived in front of area 27 of anchoring part 12, guide tube 97 with its fingers 98 is extended out of outer channel 92, whereupon fingers 98 enter end 27 of the anchoring part, while the anterior outlet end 93 of outer cannula 92 is held in the vicinity of end 27 of anchoring part 12. Insertion of guide tube 97 with its fingers 98 takes place with the guidance of endosphincter 11 until its expanded area 22, 23 is located behind constriction 92 of anchoring part 12. Then guide tube 97 together with outer cannula tube 92 with retention of valve body 13, by means of stop 94 of inner cannula tube 95, is retracted in the direction of arrow C. Fingers 98 of guide tube 97 are released in this position from outer cannula tube 92 and can expand radially outward under the pressure exerted by valve body 13, whereupon valve body 13, initially with its end 22, is stowed behind area 32 of anchoring part 12. Outer cannula 92 and guide tube 97 are retracted until the entire valve body 13 is removed from them, lies freely in urethra 3, and is only held in place by anchoring part 12 in the manner described above. The insertion elements are then removed from the urethra.

The endosphincter according to the invention can then be reused in the manner described.

We claim:

1. Artificial endosphincter for the urethra, with a retaining part and a valve body that can be secured by the latter in the urethra, with a valve that can be operated manually from the outside by exerting pressure, wherein the retaining part has a cylindrical main body with a first diameter D, and at one end thereof, a likewise cylindrical end section with a smaller second diameter d, and wherein said main body of said retaining part and said cylindrical end section thereof have an expanding retaining area for said valve body permanently connecting them together and wherein the retaining part has openings in its jacket wall to secure said valve body in the urethra.

2. Endosphincter according to claim 1, wherein said retaining area has the shape of a shoulder.

3. Endosphincter according to claim 1, wherein said retaining area has an expanding section that expands funnelwise from said end section and a reduced section that tapers in an arcuate fashion from said main body to said expanding section.

4. Endosphincter according to claim 3, wherein an intermediate section that expands partially conically is provided between said expanding section and said tapered section.

5. Endosphincter according to claim 1, wherein said retaining part has rhomboid openings in its insertion configuration.

6. Endosphincter according to claim 1, wherein said retaining part is designed as a coil spring.

7. Endosphincter according to claim 1, wherein said retaining part consists of a shape memory alloy such as Nitinol to secure said valve body in the urethra.

8. Endosphincter according to claim 1, wherein said retaining part and said valve body are connected permanently with one another in such fashion that they cannot be separated from one another without damage.

9. Endosphincter according to claim 1, wherein said retaining part and said valve body are releasably connected with one another.

10. Endosphincter according to claim 1, wherein said retaining part has a low-temperature configuration with small diameters and a high-temperature configuration above a temperature clearly below 37° with larger diameters than the low-temperature configuration.

11. Endosphincter according to claim 1, wherein said retaining part is self-expanding with a temperature increase above a transition temperature that is clearly below 37° C.

12. Endosphincter according to claim 1, wherein said valve body has a said retaining area adapted to retaining part.

13. Endosphincter according to claim 12, wherein said retaining area of said valve body is designed to be elastic in the radial direction.

14. Endosphincter according to claim 1, wherein said valve body has a main body that is tubular and cylindrical and extends from said retaining area, with a smaller diameter than retaining area (20).

15. Endosphincter according to claim 14, wherein said cylindrical main body has a diameter on the order of second diameter d of said retaining part and said retaining area has a diameter on the order of the first diameter of said retaining part.

16. Endosphincter according to claim 14, wherein said valve is formed in an end of cylindrical main body that faces away from said retaining area.

17. Endosphincter according to claim 14, wherein said cylindrical main body is provided with sealing lips near said retaining area (20).

18. Endosphincter according to claim 17, wherein said sealing lips extend radially outward approximately over said retaining area.

19. Set for releasable closure of the urethra comprising a retaining part, a valve body that can be secured in the urethra by said retaining part and a device for introduction of said valve body into the urethra, wherein said retaining part has a cylindrical main body with a first diameter D and, at one end thereof, a likewise cylindrical end section with a smaller second diameter d, and wherein said main body of retaining part and said end section thereof have a retaining area for said valve body that expands and permanently connects them together, and wherein said device for introduction of said valve body has a stop as a backing device for said valve body and an outer cannula tube surrounding said stop and receiving said valve body, said cannula being capable of being retracted relative to said stop to release the valve body from the cannula tube.

20. Set according to claim 19, wherein the diameter of the anterior end of said cannula tube is smaller than diameter d of said end section of the retaining part.

21. Set according to claim 20, further comprising a guide tube located inside said outer cannula tube that surrounds the valve body, said guide tube being extendable out of said outer cannula tube, said guide tube also being split at its free end into flexible fingers whose free ends are bent toward one another.

22. Method for introducing an endosphincter into the urethra, comprising the steps of providing a device having introducing elements for introducing the endosphincter into the urethra through the urethral opening, said introducing elements receiving the endosphincter consisting of a valve body and a retaining part permanently connected therewith, introducing said introducing elements into the urethra up to the vicinity of the pelvic floor and then pulling backward in the direction of the urethral opening relative to a steadying device for the endosphincter an outer cannula tube holding the endosphincter as part of the introducing elements, whereupon a retaining part initially emerges from the outer cannula tube and, because of its intrinsic elasticity, expands radially at human body temperature and becomes retained in the vicinity of the pars membranacea of the urethra and as the cannula tube is pulled further backward, the entire endosphincter is opened.

23. Method according to claim 22, wherein, for introduction of the retaining area of the valve body into the retaining area of the retaining part, a forward end area of an outer cannula tube of the introducing element, said end area receiving the valve body, is introduced into the tapered area of the retaining part and then the valve body is pushed by its retaining area into the retaining part.

24. Method according to claim 22, wherein, in order to introduce the retaining area of the valve body into the retaining area of the retaining part following introduction of the cannula tube containing the valve body up to a point in front of the tapered end section of the retaining part, elastic areas bent toward one another in the free end area of a guide tube surrounding the valve body and located within the cannula tube are pushed out of the cannula tube and introduced into the tapered end area of the retaining part together with the valve body until the retaining area of the valve body reaches the retaining area of the retaining part, and that the cannula tube and the guide tube are then pulled backward relative to the steadying device so that the retaining area of the valve body is initially released within the retaining area of the retaining part and the entire valve body is then released in the urethra.

25. Method according to claim 22, wherein the introduction of the introducing elements and the removal of the retaining part and/or the valve body are performed under an endoscope.

26. Method for introduction of an artificial endosphincter into the urethra, comprising the steps of providing a device having introducing elements, containing a retaining part for introduction elements, containing a retaining part, for introduction of the endosphincter into the urethra, introducing said introducing elements through the urethral opening into the urethra up to the vicinity of the pelvic floor and releasing in the vicinity of the pelvic floor an outer cannula tube containing the retaining part, while backing the retaining part with a steadying device, so that the retaining part, by elastic radial expansion at body temperature, is retained in the vicinity of the pars membranacea of the urethra, removing said introducing elements for the retaining part, introducing introducing elements, containing a valve body, of a device for the introduction of the valve body through the urethral opening into the urethra up to a point in front of an outer tapering end section of the retaining part so that a retaining section of the valve body is introduced through the tapered end section of the retaining part into a retaining area of the retaining part.

* * * * *